(12) United States Patent
Belz et al.

(10) Patent No.: US 10,578,523 B2
(45) Date of Patent: Mar. 3, 2020

(54) PARTICLE MIXING

(71) Applicant: Roche Molecular Systems, Inc., Pleasanton, CA (US)

(72) Inventors: Renato Belz, Rothenburg (CH); Willem Mulder, Baar (CH); Christopher Newhouse, Carmel, IN (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 768 days.

(21) Appl. No.: 14/946,417

(22) Filed: Nov. 19, 2015

(65) Prior Publication Data

US 2016/0139009 A1 May 19, 2016

(30) Foreign Application Priority Data

Nov. 19, 2014 (EP) ..................................... 14193860

(51) Int. Cl.
*G01N 1/30* (2006.01)
*G01N 1/31* (2006.01)
(Continued)

(52) U.S. Cl.
CPC ............ *G01N 1/30* (2013.01); *B01F 11/0051* (2013.01); *B01L 3/505* (2013.01); *G01N 1/31* (2013.01); *B01L 2200/0647* (2013.01); *B01L 2300/044* (2013.01); *B01L 2300/123* (2013.01); *B01L 2400/0481* (2013.01); *G01N 1/405* (2013.01); *G01N 2035/00534* (2013.01)

(58) Field of Classification Search
None
See application file for complete search history.

(56) References Cited

U.S. PATENT DOCUMENTS 3,819,158 A 6/1974 Sharpe et al.
4,610,684 A 9/1986 Knox et al.
(Continued)

FOREIGN PATENT DOCUMENTS

EP 2447352 B1 12/2014
KR 20110135102 A 12/2011
(Continued)

OTHER PUBLICATIONS

Sepmag(r): The Basic Guide for re-suspending magnetic beads, Aug. 25, 2013, XP055520775, Retrieved from the Internet URL: https://cdn2.hubspot.net/hub/213437/file-268011004.pdf?t+1506590170267 (retrieved on Nov. 2, 2018).

*Primary Examiner* — Robert T. Crow
(74) *Attorney, Agent, or Firm* — David J. Chang

(57) ABSTRACT

A method of separating an analyte from a biological sample is described. The method comprises providing particles capable of binding said analyte when present in a solution in a container, said container comprising walls, wherein at least a part of said walls is flexible. The particles are suspended in the solution by exerting a force on the flexible part of the walls of the container more than one time. An aliquot of the suspended particles is then removed from the container. The removed aliquot is dispensed into a sample, and the sample is incubated under conditions suitable to immobilize said analyte on the particles. The particles with the bound analyte are then separated from other material and at least part of the biological sample is removed.

7 Claims, 5 Drawing Sheets

(51) Int. Cl.
*B01L 3/00* (2006.01)
*B01F 11/00* (2006.01)
*G01N 35/00* (2006.01)
*G01N 1/40* (2006.01)

(56) References Cited

U.S. PATENT DOCUMENTS

| | | |
|---|---|---|
| 5,910,288 A | 6/1999 | Schembri |
| 6,562,568 B1 | 5/2003 | Kleiber et al. |
| 7,077,559 B2 | 7/2006 | Hlavinka et al. |
| 2005/0082204 A1 | 4/2005 | Schwartz et al. |
| 2008/0003564 A1* | 1/2008 | Chen ............... B01L 3/502 435/5 |
| 2008/0186802 A1 | 8/2008 | Bungay et al. |
| 2009/0021728 A1* | 1/2009 | Heinz ............... B01F 11/0045 356/244 |
| 2009/0311733 A1* | 12/2009 | Korpela ............... B03C 1/01 435/29 |
| 2009/0325282 A1 | 12/2009 | Bungay, III |
| 2016/0139009 A1 | 5/2016 | Belz et al. |

FOREIGN PATENT DOCUMENTS

| | | |
|---|---|---|
| WO | 0015328 A1 | 3/2000 |
| WO | 2007064635 A1 | 6/2007 |
| WO | 2008104916 A2 | 9/2008 |
| WO | 2008104916 A3 | 9/2008 |

* cited by examiner

PARTICLE MIXING

CROSS-REFERENCE TO RELATED APPLICATIONS

This application claims the benefit of priority to European Application No. EP 14193860.5, filed Nov. 19, 2014, the content of which is incorporated by reference herein in its entirety.

FIELD OF THE INVENTION

The present invention relates to systems and methods to separate and analyze biological molecules.

BACKGROUND OF THE INVENTION

Diagnostic assays for detecting or measuring analytes often require at least partial purification of the analyte. One method commonly used in analytical assays such as immunoassays or nucleic acid testing involves binding of the analyte either directly or indirectly to a particle. Thus, particles capable of either directly or indirectly binding the analyte have to be provided to the sample to be tested. Particles may be provided in a solid form, but preferably are provided as a suspension of particles in a solution, generally by transferring an aliquot of the solution comprising the suspended particles using a pipetting device.

When such analyte-binding particles are provided as a suspension in a solution, care has to be taken that the suspension is homogenous when an aliquot is aspirated by the pipetting device for transfer to the sample. Commonly, containers comprising a solution of such suspended particles are subjected to shaking of the container using a shaking mechanism. The homogeneity of the suspended particle solution may be affected by the shaking movement itself carried out by the shaking mechanism and by the design of the container.

SUMMARY OF THE INVENTION

The present invention relates to a method of separating an analyte from a biological sample. The method comprises providing particles capable of binding said analyte when present in a solution in a container, said container comprising walls, wherein at least a part of said walls is flexible. The particles are suspended in the solution by exerting a force on the flexible part of the walls of the container more than one time. An aliquot of the suspended particles is then removed from the container. The removed aliquot is dispensed into a sample, and the sample is incubated under conditions suitable to immobilize said analyte on the particles. The particles with the bound analyte are then separated from other material and at least part of the biological sample is removed.

The present invention further relates to a system for separating an analyte comprising a container. The container comprises walls. At least a part of the walls is flexible. The container comprises particles in a solution. The system also comprises a separation station. The system further comprises a movable mechanical device functionally coupled to the flexible walls being part of the walls of the container, and a control unit configured to control the movable mechanical device such that it exerts pressure on the flexible walls being part of the walls of the container to suspend the particles in the container.

DETAILED DESCRIPTION OF THE INVENTION

Figure 1:
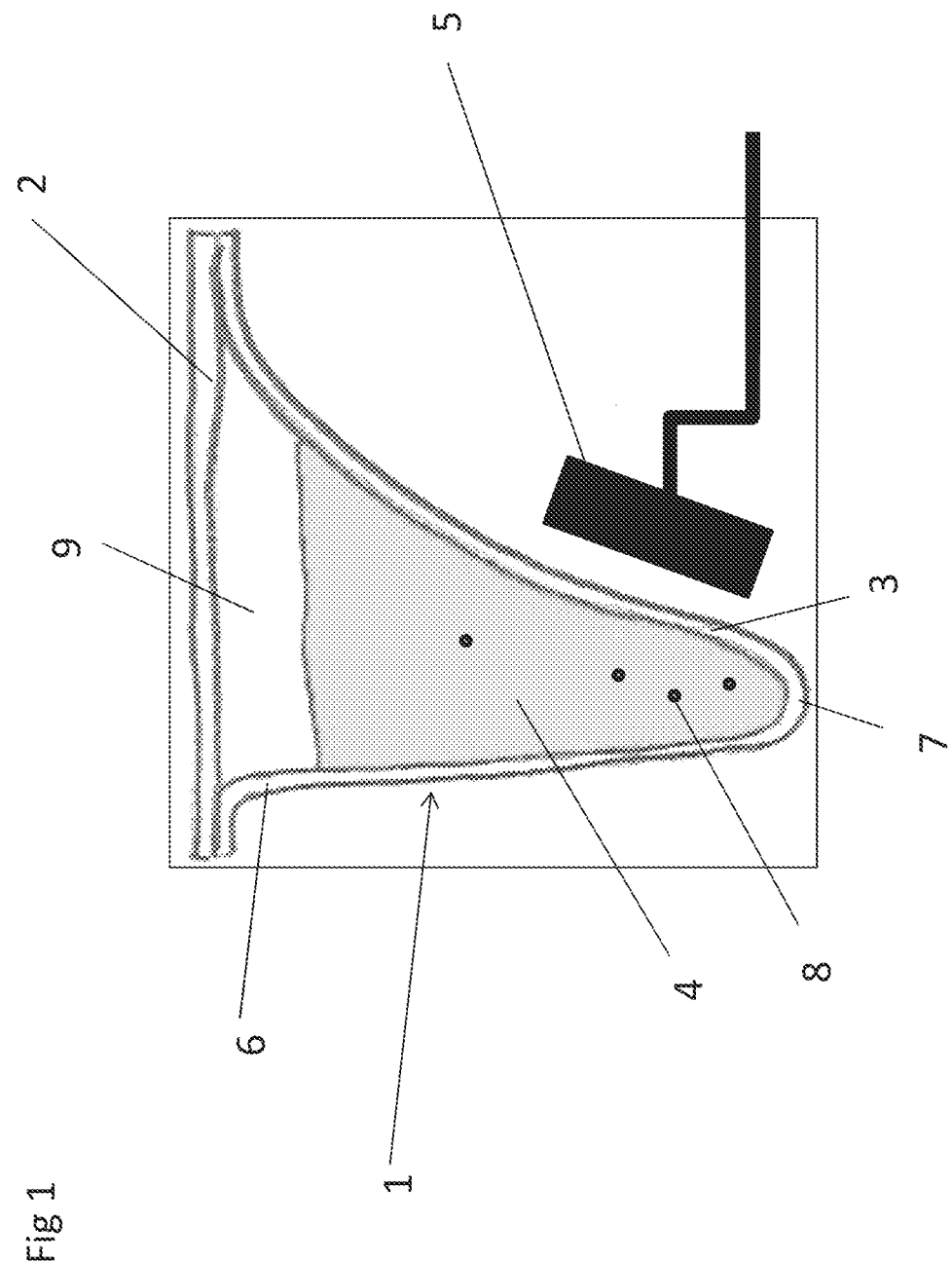
FIG. 1 shows a side view of the container of the present invention.

The present disclosure relates to a method for mixing particles capable of binding a biological molecule. The method comprises the steps of providing particles suspended in a solution in a container, said container comprising walls, wherein at least a part of said walls is flexible, and suspending the particles by exerting a force on the flexible part of said walls of the container more than one time.

The term "analyte" as used herein may be any type of analyte which is of interest for detection, and the detection thereof is indicative of a diagnostic status of an organism. In one specific embodiment, the analyte is a biological molecule. The organism can be animal or, in one embodiment, human. "Biological molecules" may be proteins, polypeptides, antibodies or nucleic acids. In one embodiment, the analyte is a target nucleic acid. A "target nucleic acid" is a polymeric compound of nucleotides as known to the expert skilled in the art. "Target nucleic acid" is used herein to denote a nucleic acid in a sample which should be analyzed, i.e. the presence, non-presence and/or amount thereof in a sample should be determined. The target nucleic acid may be a genomic sequence, e.g. part of a specific gene, or RNA. In other embodiments, the target nucleic acid may be viral or microbial.

The analyte may be present in a liquid sample, or it may be present as a solid sample affixed to a support. Solid samples may include tissue.

The term "sample", as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays like e.g. clinical chemistry assays, immunoassays, coagulation assays, nucleic acid testing, etc. The term "sample" as used herein is therefore not only used for the original sample but also relates to a sample which has already been processed (pipetted, diluted, mixed with reagents, enriched, separated, having been purified, having been amplified etc).

In in-vitro diagnostics, the analyte is often enriched by separation from other material present in the sample. This enrichment is beneficial for the sensitivity and the quality of a detection method. One established separation method comprises binding of a biological molecule of interest to a solid support. The term "solid support" as used herein relates to any type of solid support to which the analyte is capable of binding, either directly and non-specifically by adsorption, or indirectly and specifically. Indirect binding may be binding of an analyte to an antibody immobilized on the solid support, or binding of a tag to a tag binding compound, e.g. binding of 6×His tags to Ni-chelate, or avidin binding to streptavidin coated beads. Solid support material may be a polymer, or a composition of polymers. Specifically, particles may be used as solid support material. Examples of particles include latex particles, magnetic silica particles, metal particles, magnetic glass particles. Other types of solid supports include glass fibers, glass fiber filters, filter paper, etc., while the solid support material is not limited to these materials.

When using particles as solid support for separation of an analyte, they may be added in dry form to a sample. They may also be provided suspended in a solution. When providing the particles suspended in a solution, the reproducibility of the method is affected by the homogeneity of the suspension. It is, therefore, important to mix the solution comprising the suspended particles just before transferring an aliquot of this solution to the sample. An improved homogenous solution is obtained by the present invention by providing the particles suspended in a solution in a container which has walls of which at least a part is flexible. The homogenous solution is obtained by exerting a force on the flexible part of the walls of the container more than one time. The force causes the liquid inside the container to move, thereby obtaining a mixing of the suspended particles, resulting in an improvement of the homogeneity of the suspended particles.

In one specific embodiment, the force is exerted onto a section located in the bottom half of said container, wherein said section is located in the flexible part of said walls of said container.

In one embodiment of the invention, exerting of a force is achieved by a movable mechanical device. In one specific embodiment, said exerting of a force is achieved automatically by a movable mechanical device. In one embodiment, such a movable mechanical device may be a device with a tool configured to exert a force on a flexible part of the container. The surface contacting the container may be flat or rounded. The force may be exerted e.g. by hitting or clapping the tool against a flexible part of the container. The movable mechanical device may be moved manually to exert a force on a flexible part of the container. For automation, the tool may be connected to a robotic arm. In either case, the force may be exerted by hitting the tool against a flexible part of the container.

In another embodiment, the force may be exerted manually. This may be achieved by squeezing the bottom part of the container with several fingers, which then results in suspending the particles to obtain an improved homogeneity of the suspension of particles in the solution.

In one specific embodiment of the invention described herein, magnetic particles are used.

The present disclosure further relates to a container comprising walls, wherein at least a part of said walls is flexible. The container comprises a solution comprising particles. The container is held in a frame, wherein said frame comprises an open bottom configured to permit access to the flexible part of the walls such that a force can be exerted on the flexible part of the walls of the container.

The term "frame" relates to an outer supporting structure for the container. In one embodiment, the container is affixed to the frame. The term "affixed" relates to a physical attachment of the container to the frame. The container may be affixed by gluing or may be affixed by applying heat. Other known types of affixing a container to a frame can be used. The container is, thus, not integrally formed with the frame. Since the frame structurally supports the container, it is made of a different material than the container. In a specific embodiment, the frame is made of a stiff material.

The frame has an opening to permit access to a flexible part of the walls such that a force can be exerted on the flexible part of the walls of the container. In a specific embodiment, the frame has an open bottom to permit access to a flexible part of the walls such that a force can be exerted on the flexible part of the walls of the container. In further specific embodiment, the frame has two long and two short walls, whereby one edge of each long side wall contacts one edge of a short side wall. In a further specific embodiment, one of the long side walls extends from the top end of the frame to a level above the bottom of the other long side wall. Thus, from the top downwards, one long side wall is shorter than the other side wall. This makes access for the movable mechanical tool easier. In one embodiment, the frame has an open top end.

In one embodiment, the container is closed on the bottom end and comprises an open top end. The closed bottom end allows the container to hold the solution. The open top end allows the container to be filled with solution and also makes it possible to remove the solution or an aliquot thereof.

In one embodiment, the frame and the container comprise a common lid on the top end. The lid, thus, covers the open top end of the container and the open top end of the frame. In a specific embodiment, the lid comprises at least one seal, wherein said seal is penetrable by a pipette tip or a needle. The lid may be mounted on the frame and container after the solution is filled into the container. The lid protects the solution in the container from spilling or from contamination from the outside. In order to be able to remove an aliquot of the suspended particles from the lidded container and frame, at least one seal is comprised on the lid which is configured to be penetrable for a pipette tip or a needle.

A pipette tip is a tip, more specifically a disposable tip, which is reversibly or fixedly attached to a pipetting device. A needle is a non-disposable tip, specifically a steel needle, which may be reversibly of fixedly attached to a pipetting device. These devices are used for pipetting. The term "pipetting" is herein used to indicate aspirating, i.e. withdrawing, a volume of liquid in a first step and dispensing a volume of liquid in a second step, wherein the volume of dispensed liquid may be the same or different from the volume of aspirated liquid and wherein intermediate aspirating and/or dispensing steps may or may not occur between the first step and the second step. A pipetting device is an automated device which is configured to aspirate and dispense liquids using pipette tips or needles. Such devices are well known in the art. One pipetting device may be able to engage one or more tips or needles, or may have one or more tips or needles fixedly attached to it. A penetrable seal is a seal which may be penetrated by a pipette tip or needle. The seal may be frangible, i.e. the seal is broken by the pipette tip or needle and will, thereafter, not re-seal. In another embodiment, the seal is resealable. Examples of such resealable seals are seals made of rubber. In one specific embodiment, the lid comprises at least one split septum. A split septum is a seal which is pre-slit. Such seals are known in the art. They have the advantage that they can be penetrated more easily than a septum which is not pre-slit. On the other hand, the split septum closes again after the pipette tip or needle has been withdrawn, thus reducing the risk of spillage or contamination of the contents of the container.

In one specific embodiment of the container herein described, the material of the container is a rubber-like material. Such a material provides flexibility to the walls, durability and makes it possible to visually control the mixing and homogeneity of the particles suspended in the solution contained in the container.

The present invention relates to a method of separating an analyte from a biological sample. The method comprises providing particles capable of binding said analyte when present in a solution in a container, said container comprising walls, wherein at least a part of said walls is flexible. The particles are suspended in the solution by exerting a force on the flexible part of the walls of the container more than one time. An aliquot of the suspended particles is then removed from the container. The removed aliquot is dispensed into a sample, and the sample is incubated under conditions suitable to immobilize said analyte on the particles. The particles with the bound analyte are then separated from other material and at least part of the biological sample is removed.

As mentioned above, in in-vitro diagnostics, an analyte is often enriched by separation from other material present in the sample. This enrichment is beneficial for the sensitivity and the quality of a detection method. One established separation method comprises binding of a biological molecule of interest to a solid support. For this, particles capable of binding the analyte are provided in a container. Thus, the container holds a suspension of such particles. In order to dispense a controlled amount of particles in an aliquot of the suspension to a sample, the particles should be present as a homogenous suspension in the solution contained in the container. The more homogenous the suspension is, the more reliable and precise the data are which are eventually obtained from detecting or measuring the analyte following analyte separation. In the present invention, the homogenous suspension is achieved by using a container comprising walls, wherein at least a part of said walls is flexible, and by exerting a force on the flexible part of the walls of the container more than one time. By this, a homogenous suspension of particles can be obtained in the solution. An aliquot can then be removed from the solution in the container and dispensed into the sample. This ensures that an aliquot of a certain volume will always contain the same amount of particles as the same volume of a second aliquot taken from the same solution contained in the container. Following dispensing of the aliquot, the sample is incubated with the particles under conditions suitable to immobilize said analyte on the particles. Such conditions are well known in the art. Once the analyte is immobilized, the particles with the bound analyte are then separated from the other material present in the solution comprising the sample, and at least a part of the sample is removed.

The term "aliquot" as used herein relates to a portion of a solution.

In one embodiment of the method described herein, the method additionally comprises the step of washing said particles with the bound analyte one or more times following separation from other material. The term "washing" is understood to mean that a volume suitable solution is added to the particles with the bound particles. Suitable washing solutions are wash buffers. A "wash buffer" is a fluid that is designed to remove undesired components, especially in a purification procedure. Such buffers are well known in the art. In the context of the purification of nucleic acids, the wash buffer is suited to wash the solid support material in order to separate the immobilized nucleic acid from any unwanted components. Thus, in one embodiment, the analyte is a nucleic acid. The wash buffer may, for example, contain ethanol and/or chaotropic agents in a buffered solution or solutions with an acidic pH without ethanol and/or chaotropic agents as described above. Often the washing solution or other solutions are provided as stock solutions which have to be diluted before use.

At the end of the washing step, at least a part of the washing solution is separated and removed from the particles. In one specific embodiment, the washing step is repeated at least once.

In one embodiment, the method additionally comprises eluting the analyte from said particles following separation or washing. The term "eluting" relates to the release of the bound analyte from the particles. Commonly, elution is performed using a suitable elution buffer. An "elution buffer" in the context of the invention is a suitable liquid for separating analyte from the particles. Such a liquid may e.g. be distilled water or aqueous salt solutions, such as e.g. Tris buffers like Tris HCl, or HEPES, or other suitable buffers known to the skilled artisan. The pH value of such an elution buffer may be alkaline or neutral in the case that the analyte is a nucleic acid. Said elution buffer may contain further components such as e.g. chelators like EDTA, which stabilizes the isolated nucleic acids by inactivation of degrading enzymes.

The elution may require elevated temperatures. As a non-limiting example, in case the analyte is a nucleic acid, the elution is carried out at a temperature between 70° C. and 90° C., more specifically at a temperature of 80° C.

In one embodiment of the method, the force is exerted mechanically. In a specific embodiment, the force is exerted by an operator by hand. More specifically, the operator may squeeze and release the flexible part repeatedly by hand, thus exerting the mechanical force.

In another embodiment, the mechanical exerting is automated. In a specific embodiment, the automation is achieved by a movable mechanical device. In a more specific embodiment, the movable mechanical device may be a device configured to hit or squeeze the flexible part of the container. One specific embodiment of such a movable mechanical device may be a gripper or hammer head connected to a robotic arm.

In one embodiment of the invention, said removing of an aliquot from the container is performed during exerting of force on the flexible part of the walls of the container. This has the advantage that the particles are more homogenously suspended during the exertion of a force, and that, thus, the aliquot contains a homogenous suspension of particles, thus increasing the reliability and quality of the detection or measurement of the analyte, which is ultimately done.

The present invention further relates to a system for separating an analyte comprising a container. The container comprises walls. At least a part of the walls is flexible. The container comprises particles in a solution. The system also comprises a separation station. The system further comprises a movable mechanical device functionally coupled to the flexible walls being part of the walls of the container, and a control unit configured to control the movable mechanical device such that it exerts pressure on the flexible walls being part of the walls of the container to suspend the particles in the container.

Systems for separating an analyte using particles capable to bind an analyte are well known in the art. Such systems comprise a separation station. When using particles which are not magnetic, a suitable separation station may comprise a filter unit which is configured to retain the particles and a vacuum system which is configured to remove the liquid from the particles when a vacuum is applied. Another embodiment of such a separation station is a centrifugation unit which is configured to pellet the particles within a vessel containing the sample and the particles with bound analyte, thus, separating the particles from the solution present in the container. Another type of separation station which is commonly used is a magnetic separation station configured to retain magnetic particles with bound analyte at the bottom or on the walls of one or more vessels containing a sample and particles with bound analyte. All of these separation stations are configured to separate particles with bound analyte from the sample and the liquid component of the particle suspension, and to remove the sample and other liquid after binding the analyte to the particles. The particles can then be either washed and recovered, or directly recovered. As mentioned before, the particles thus separated from the other material in the sample may then additionally be washed to remove contaminants, and/or the analyte may finally be eluted from the particles. The thus obtained analyte may then be detected or measured in the same or in a different system.

The system of the present invention comprises a movable mechanical device functionally coupled to the flexible walls being part of the walls of the container. The term "functionally coupled" is understood to mean that the movable mechanical device interacts with the flexible part of the walls in a manner that permits obtaining a homogenous suspension of the particles in the solution contained in the container.

The system comprises a control unit (CU) for controlling the analyzer. Such a control unit may be a separate unit or may be an integral part of an analytical instrument. The control unit controls the analyzer in a way that the necessary steps for the assay protocols are conducted by the analyzer. That means the control unit e.g. instructs the analyzer to conduct certain pipetting steps to mix the sample with reagents or the control unit controls the analyzer to incubate the sample mixtures for a certain time and so on. The control unit receives information from the data manager which test has to be done with a certain sample and based thereon determines the steps the analyzer (and maybe also a sample preparation unit) has to perform. In certain embodiments the control unit might be integral with the data management unit or may be embodied by a common hardware.

In one embodiment of the system of the present invention, the container is held in a frame, wherein said frame comprises an opening at the bottom of the container. In a specific embodiment, the frame and the container are covered by a lid. In a more specific embodiment, the lid comprises at least one opening. This opening can permit access to the contents of the container In an even more specific embodiment, a resealable seal covers said opening. Such seals are made of a flexible material, e.g. rubber or a thermoplastic material. They prevent contamination or spillage of the contents.

In one embodiment of the system, it further comprises a pipetting device. In a more specific embodiment, the pipetting device and said movable mechanical device are functionally coupled and said control unit is configured to control the movable mechanical device and the pipetting device such that the movable mechanical device exerts a force on the flexible walls being part of the walls of the container to suspend the particles in the container for at least the same time period that the pipetting system requires to aspirate an aliquot of the solution comprising the particles, and said movable mechanical device exerts a force on the flexible walls being part of the walls while the pipetting system aspires an aliquot of the solution comprising particles.

The term "the pipetting device and said movable mechanical device are functionally coupled" means that their pipetting function and exerting a force functions are coordinated.

EXAMPLES

FIG. 1 shows a container (1) comprising a closed bottom end (7) and an open top end (9). The open top end (9) of the container (1) is covered by a lid (2). The container (1) comprises walls (6). At least a part of walls (6) are flexible walls (3). The container (1) contains a solution (4) in which particles (8) are suspended. A force can be exerted on the flexible part (3) of the walls (6) of the container (1) by a movable mechanical device (5) to achieve homogenous mixing of the particles (8).

Figure 2:
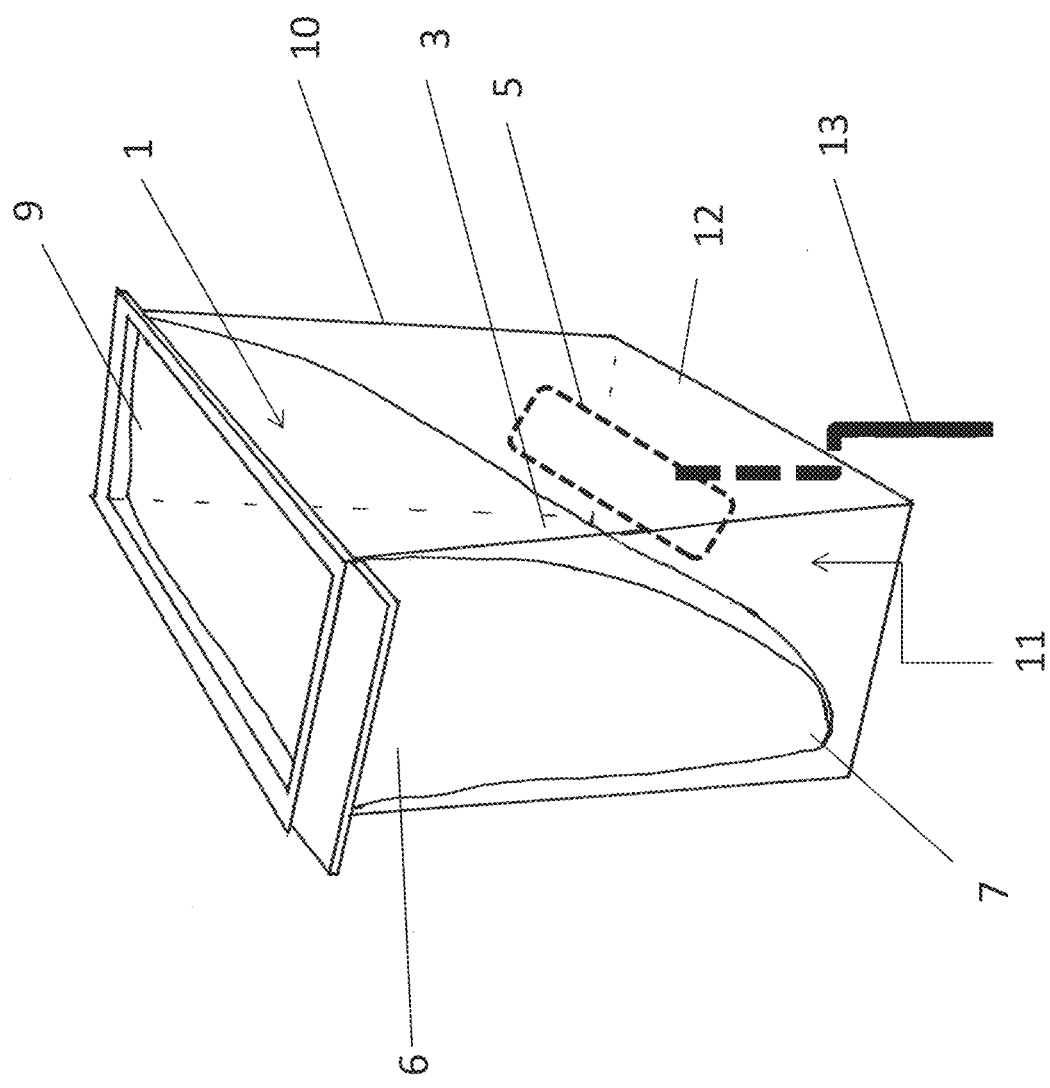
FIG. 2 shows a lateral view of the container of the present invention.

FIG. 2 shows the container (1) comprising walls (6), at least part of which comprise flexible walls (3). The container (1) further comprises a closed bottom end (7) and an open top end (9). Like in FIG. 1, the container (1) contains a solution (4) in which particles (8) are suspended (not shown in this Figure). The container (1) is held in a frame (10). Frame (10) comprises an opening (11) on the bottom (12). The movable mechanical device (5) can access the flexible walls (3) of container (1) through the opening (11) of the frame (10). In one specific embodiment, the movable device (5) may comprise a robotic arm (13).

Figure 3:
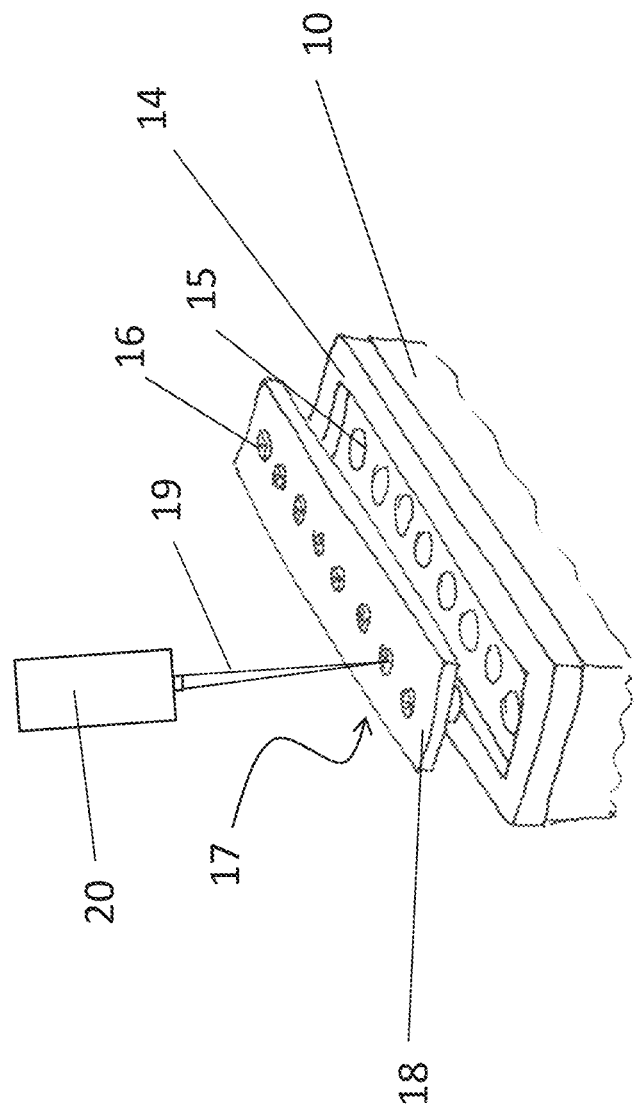
FIG. 3 shows that lid that covers the container and frame.

FIG. 3 shows a lid (14) which covers container (1) (not shown) and frame (10). In one specific embodiment, the lid (14) comprises openings (15) in which a resealable seal (16) can be set. FIG. 3 shows, as a specific embodiment, a septum strip (17) comprising a base (18) and multiple septa (16). Each resealable septum (16) is penetrable for a pipette tip (19) which is attached to a pipetting device (20). The pipette tip (19) may be a disposable tip releasably attached to the pipetting device (20) or a needle affixed to the pipetting device (20).

Figure 4:
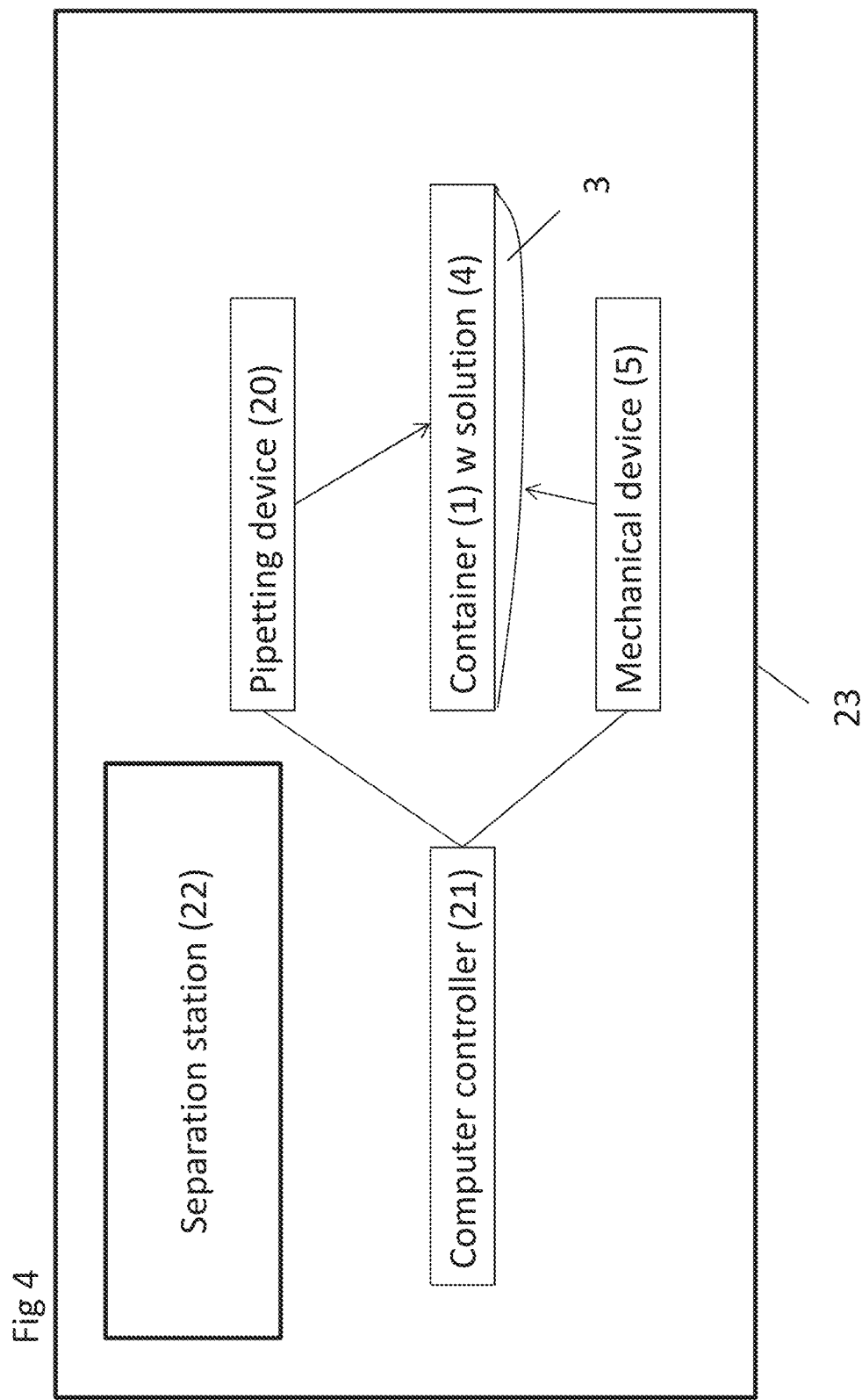
FIG. 4 is a schematic of the system of the present invention.

FIG. 4 is a schematic of a system (23) comprising a separation station (22), a pipetting device (20) and a movable mechanical device (5). The system (23) further comprises a container (1) with a solution (4) comprising particles (8). A control unit (21) comprised in the system (23) is configured to control the movable mechanical device (5) and the pipetting device (20) such that the movable mechanical device (5) exerts a force on the flexible part (3) of the walls (6) of the container (1) to suspend the particles (8) (not shown in this Figure) in the container (1) for at least the same time period that the pipetting device (20) requires to aspirate an aliquot of the solution (4) comprising the particles (8) (not shown in this Figure).

Figure 5:
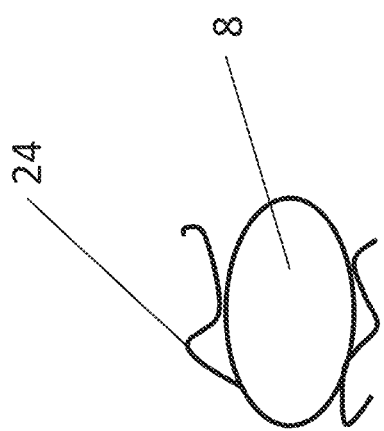
FIG. 5 is a schematic representation of a particle to which an analyte is bound.

FIG. 5 is a schematic representation of a particle (8) to which an analyte (24) is bound.

The invention claimed is:
1. A method of separating an analyte from a biological sample comprising
providing particles capable of binding said analyte when present in a solution in a container, said container comprising walls, wherein at least a part of said walls is flexible,
suspending the particles in said solution by exerting a force on the flexible part of the walls of the container more than one time, removing an aliquot of the suspended particles from the container with a pipetting device during exertion of force on the flexible part of the walls of the container, dispensing said aliquot into a sample incubating the sample under conditions suitable to immobilize said analyte on the particles, separating said particles with the bound analyte from other material and removing at least part of the biological sample.

2. The method of claim 1, additionally comprising washing said particles with the bound analyte one or more times following separation from other material.

3. The method of claim 2, additionally comprising eluting the analyte from said particles following separation or washing.

4. The method of claim 1, wherein said force is exerted mechanically.

5. The method of claim 4, wherein said force exerted mechanically is automated.

6. The method of claim 4, wherein a movable mechanical device exerts a force on said container.

7. The method of claim 6, wherein the pipetting device and the movable mechanical device are functionally coupled.

* * * * *